US010035022B2

(12) United States Patent
Busch et al.

(10) Patent No.: US 10,035,022 B2
(45) Date of Patent: Jul. 31, 2018

(54) RATE-ADAPTIVE HEART STIMULATOR AND ACTIVITY SENSOR

(71) Applicant: Biotronik SE & Co. KG, Berlin (DE)

(72) Inventors: Ulrich Busch, Berlin (DE); Andreas Neumann, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 15/170,895

(22) Filed: Jun. 1, 2016

(65) Prior Publication Data

US 2016/0361548 A1    Dec. 15, 2016

(30) Foreign Application Priority Data

Jun. 9, 2015    (DE) .................. 10 2015 109 037

(51) Int. Cl.
*A61N 1/00*       (2006.01)
*A61N 1/365*      (2006.01)
*A61N 1/375*      (2006.01)
*A61B 5/11*       (2006.01)
*A61N 1/362*      (2006.01)
(Continued)

(52) U.S. Cl.
CPC .......... *A61N 1/36542* (2013.01); *A61B 5/042* (2013.01); *A61B 5/1118* (2013.01); *A61B 5/686* (2013.01); *A61B 5/6869* (2013.01); *A61N 1/3627* (2013.01); *A61N 1/36578* (2013.01); *A61N 1/3702* (2013.01); *A61N 1/3704* (2013.01); *A61N 1/3756* (2013.01); *A61B 5/02444* (2013.01); *A61B 5/0456* (2013.01);
(Continued)

(58) Field of Classification Search
CPC .............. A61N 1/3756; A61N 1/36542; A61N 1/3702; A61N 1/37205; A61N 1/3627; A61N 1/3704; A61N 1/36578; A61B 5/042; A61B 5/1118; A61B 5/686; A61B 5/6869; A61B 5/02444; A61B 5/0456; A61B 2562/0219
See application file for complete search history.

(56) References Cited

U.S. PATENT DOCUMENTS 4,926,863 A    5/1990  Alt
5,031,615 A    7/1991  Alt
(Continued)

FOREIGN PATENT DOCUMENTS

WO    2001056651 A1    8/2001
WO    2015100071 A1    7/2015

OTHER PUBLICATIONS

German Search Report received in Application Serial No. DE102015109037.6 dated Mar. 2, 2016, 7 pages.
(Continued)

*Primary Examiner* — Mallika D Fairchild
(74) *Attorney, Agent, or Firm* — ARC IP Law, PC; Joseph J. Mayo (57) ABSTRACT

Embodiments include a leadless implantable heart stimulator (that includes an acceleration sensor, wherein the acceleration sensor delivers an acceleration signal as an output signal. The acceleration sensor is connected to an activity determination unit. The activity determination unit generates an activity signal from the acceleration signal wherein the activity determination unit at least partially subtracts a component of the acceleration signal from the acceleration signal that represents an intrinsic heart movement.

6 Claims, 4 Drawing Sheets

(51) Int. Cl.
    *A61N 1/37*         (2006.01)
    *A61B 5/042*       (2006.01)
    *A61B 5/00*         (2006.01)
    A61B 5/024       (2006.01)
    A61N 1/372       (2006.01)
    A61B 5/0456     (2006.01)

(52) U.S. Cl.
    CPC ... *A61B 2562/0219* (2013.01); *A61N 1/37205* (2013.01)

(56) References Cited

U.S. PATENT DOCUMENTS

| | | |
|---|---|---|
| 5,179,947 A | 1/1993 | Meyerson et al. |
| 5,215,084 A | 6/1993 | Schaldach |
| 5,243,979 A | 9/1993 | Stein et al. |
| 5,330,510 A | 7/1994 | Legay et al. |
| 5,383,473 A | 1/1995 | Moberg |
| 5,425,750 A | 6/1995 | Moberg |
| 5,480,412 A | 1/1996 | Mouchawar et al. |
| 5,496,361 A | 3/1996 | Moberg et al. |
| 5,833,713 A | 11/1998 | Moberg |
| 7,937,148 B2 | 5/2011 | Jacobson |
| 8,543,205 B2 | 9/2013 | Ostroff |
| 2012/0095521 A1 | 4/2012 | Hintz |
| 2012/0109236 A1 | 5/2012 | Jacobson et al. |
| 2013/0079861 A1 | 3/2013 | Reinert et al. |
| 2015/0105836 A1 | 4/2015 | Bonner et al. |
| 2015/0173655 A1* | 6/2015 | Demmer ............ A61B 5/1118 600/595 |

OTHER PUBLICATIONS

European Search Report received in Application Serial No. 16166559.1-1666, dated Oct. 24, 2016, 7 pages.

* cited by examiner

RATE-ADAPTIVE HEART STIMULATOR AND ACTIVITY SENSOR

This application claims the benefit of German Patent Application DE 10 2015 109 037.6 filed on 9 Jun. 2015, the specification of which is hereby incorporated herein by reference.

BACKGROUND OF THE INVENTION

Field of the Invention

Embodiments of the invention generally relate to a leadless heart stimulator, such as an intracardial or epicardial heart stimulator, which includes an activity sensor. In addition, embodiments of the invention generally relate to an activity sensor that detects physical activity based on detected acceleration values.

Description of the Related Art

Generally, implantable heart stimulators, such as cardiac pacemakers, have a housing, in which a battery is arranged, which allows operation of the pacemaker over many years. Typically, the battery supplies power to a pacemaker controller, which is generally connected to a detection stage for heart signals and also to a stimulation pulse generator. Generally, both the stimulation pulse generator and the detection stage for heart signals are in turn connected to connectors for one or more electrode leads, which make it possible to deliver stimulation pulses generated by the stimulation pulse generator to the muscle tissue of the heart (myocardium) or to detect and to process electrical potentials in the heart.

Cardiac pacemakers of this type are typically implanted beneath a patient's collarbone and with which a connection is made to the heart via flexible electrode leads, which end in the respective heart chamber (atrium or ventricle) and are provided there with electrodes. Generally, leadless cardiac pacemakers are also used, which may be placed as a whole in a heart chamber (intracardially). Typically, cardiac pacemakers may be secured externally on the heart (epicardially).

Generally, heart stimulators to be placed on or in the heart that do not require any electrode leads, are referred to as "leadless". Within the scope of this invention, such cardiac pacemakers will therefore be referred to herein as leadless cardiac pacemakers or synonymously as heart stimulators having no electrode leads.

Typically, different operating modes and variants of cardiac pacemakers may be used and are not further explained herein. In particular, generally, a stimulation rate of a cardiac pacemaker is controlled depending on the metabolic need of a patient. Typically, rate-adaptive cardiac pacemakers of this type require a sensor for the metabolic need. Generally, possible sensor types are temperature sensors or acceleration sensors (accelerometers).

For example, U.S. Pat. No. 4,926,863, entitled "Rate Responsive Cardiac Pacemaker", to Alt, appears to describe a rate-adaptive cardiac pacemaker that includes an acceleration sensor. U.S. Pat. No. 8,543,205 B2, entitled "Temperature Sensor for a Leadless Cardiac Pacemaker", to Ostroff, appears to describe a rate-adaptive intracardial cardiac pacemaker that includes a temperature sensor. For example, U.S. Pat. No. 7,937,148 B2, entitled "Rate Responsive Leadless Cardiac Pacemaker", to Jacobson, appears to describe a rate-adaptive intracardial cardiac pacemaker that includes an acceleration sensor.

U.S. Pat. No. 5,031,615, entitled "Rate Responsive Cardiac Pacemaker", to Alt, appears to disclose a cardiac pacemaker that includes an accelerometer. For example, U.S. Pat. No. 5,215,084, entitled "Cardiac Pacemaker with Activity Sensor", to Schaldach, appears to disclose a cardiac pacemaker that includes an activity sensor for detecting physical activity of a patient. U.S. Pat. No. 5,243,979, entitled "Method and Apparatus for Implementing Activity Sensing in a Pulse Generator", to Stein et al., appears to disclose a cardiac pacemaker that includes a sensor responsive to the patient's metabolic demand. For example, U.S. Pat. No. 5,330,510, entitled "Pacemaker with Patient Effort-Controlled Frequency", to Legay et al., appears to disclose a pacemaker with accelerometers wherein each of the accelerometers is sensitive in one direction of a Cartesian coordinate system.

U.S. Pat. No. 5,383,473, entitled "Rate-Responsive Implantable Stimulation Device Having a Miniature Hybrid-Mountable Accelerometer-Based Sensor and Method of Fabrication", U.S. Pat. No. 5,425,750, entitled "Accelerometer-Based Multi-Axis Physical Activity Sensor for a Rate-Responsive Pacemaker and Method of Fabrication, and U.S. Pat. No. 5,833,713, entitled "Rate Responsive Pacemaker Having an Accelerometer-Based Physical Activity Sensor", all to Moberg, appear to disclose a rate-responsive pacemaker with a physical activity sensor.

U.S. Pat. No. 5,480,412, entitled "System and Method for Deriving Hemodynamic Signals from a Cardiac Wall Motion Sensor", to Mouchawar et al., appears to disclose a processing system and method for deriving an improved hemodynamic indicator from cardiac wall acceleration signals. U.S. Pat. No. 5,496,361, entitled "System and Method for Detecting Cardiac Arrhythmias Using a Cardiac Wall Acceleration Sensor Signal", to Moberg et al., appears to disclose implantable leads incorporating accelerometer-based cardiac wall motion sensors. U.S. Pat. No. 7,937,148, entitled "Rate Responsive Leadless Cardiac Pacemaker", to Jacobson, appears to disclose a pacemaker with an activity sensor.

BRIEF SUMMARY OF THE INVENTION

One or more embodiments of the invention include a cardiac pacemaker that may be placed intracardially or epicardially in a patient. In at least one embodiment, the cardiac pacemaker includes an acceleration sensor to determine physical activity of the patient.

One or more embodiments of the invention include an implantable cardiac stimulator having no electrode leads, or a leadless implantable cardiac stimulator, that includes an acceleration sensor that delivers an acceleration signal as an output signal. In at least one embodiment, the acceleration sensor may be connected to an activity determination unit. In one or more embodiments, the activity determination unit may generate an activity signal from the acceleration signal, wherein the activity determination unit at least partially subtracts from the acceleration signal a component of the acceleration signal attributable to, or that represents, an intrinsic heart movement.

At least one embodiment of the invention includes a method of forming an activity signal representing a physical activity. In one or more embodiments, the method may include at least one or more of the following steps:
  recording an acceleration signal,
  subtracting a signal component at least approximately representing an intrinsic heart movement, and generating an activity signal based on a difference formed by the subtracting.

One or more embodiments of the invention include the recognition that an acceleration sensor placed in or on the heart records both the intrinsic heart movement and the movement of the entire body, wherein a leadless cardiac pacemaker may track body movements, and may track intrinsic heart movements. In at least one embodiment, the acceleration signal may include signal components attributable to or represent body movements, and may include signal components superimposed by intrinsic heart movements, which may include a disturbance function. In one or more embodiments, the acceleration signal may be a sum signal of the two movement components constituted by intrinsic heart movement and body movement. In order to control the stimulation rate, by way of at least one embodiment, a separation of the two signal components may be provided. In one or more embodiments, the signal components may be separated using different methods, wherein the different methods may include a common feature of a mean value of the acceleration of the heart component that is determined.

In at least one embodiment, a stimulation rate adaptation may be performed based on an acceleration signal originating from an acceleration sensor. In one or more embodiments, the acceleration sensors include sensors that may adapt the stimulation rate of a heart stimulator. In at least one embodiment, the acceleration sensors respond quickly, may include very little stability problems, and their behavior is easily understood. By way of one or more embodiments, via an activity determination unit and via the method discussed herein, acceleration sensors may be used to adapt the stimulation rate in a heart stimulator having no electrode leads, such as a leadless heart stimulator.

In order to separate the acceleration component of the heart from the component of the body movement, in at least one embodiment, the acceleration over each cardiac cycle may be taken into account separately. In order to determine the acceleration component of the body, in one or more embodiments, the signal component of the acceleration signal attributable to the intrinsic heart movement may be subtracted from the total value of the acceleration signal.

According to at least one embodiment, the activity determination unit may determine a minimum value of the acceleration signal and may subtract the minimum value thus determined from a respective current value of the acceleration signal.

In one or more embodiments, the minimum value may be determined for example over a period of time that includes a plurality of cardiac cycles, such as a number of hours.

In at least one embodiment, the activity determination unit may integrate the acceleration signal over a predefined period of time to form an acceleration integral.

By way of one or more embodiments, the activity determination unit may integrate a respective absolute value of the acceleration signal over a predefined period of time to form an acceleration integral.

In at least one embodiment, the activity determination unit may form the acceleration integral in each case over a cardiac cycle.

In one or more embodiments, the activity determination unit may determine the minimum value from the acceleration signal during a rest phase.

In at least one embodiment, the activity determination unit may determine the minimum value from the acceleration integral during a rest phase.

In one or more embodiments, the activity determination unit may subtract the minimum value from a respective acceleration integral and may output the difference thus formed as an activity signal.

In at least one embodiment, the activity determination unit may integrate the signed acceleration signal over a predefined period of time to form an acceleration integral. In one or more embodiments, the predefined period of time may include a cardiac cycle.

According to at least one embodiment of the invention, the heart stimulator may include a control unit, wherein the control unit is connected to the activity determination unit and may detect rest phases.

In one or more embodiments, the heart stimulator may include at least one sensing unit connected to at least one electrode. In at least one embodiment, the at least one sensing unit may record electrical potential curves via the electrode as an electrocardiogram (ECG) signal and may detect signal features including intrinsic heart actions of the ECG signal characteristic, such as R waves.

In one or more embodiments, the heart stimulator may include or may form a rate-adaptive cardiac pacemaker with a control unit and a stimulation unit connected thereto. In at least one embodiment, the rate-adaptive cardiac pacemaker may control the stimulation unit based on a stimulation rate, wherein the stimulation rate is dependent on the activity signal.

One or more embodiments may include an activity detection module, wherein the activity detection module includes an acceleration sensor and an activity determination unit connected thereto. In at least one embodiment, the activity detection module may generate an activity signal from an acceleration signal formed by and/or delivered by the acceleration sensor, wherein the activity determination unit at least partially subtracts from the acceleration signal a component of the acceleration signal attributable to or that represents an intrinsic heart movement.

In one or more embodiments of the invention, the activity determination unit may perform one or more of the following two variants:

First Method Variant:

In at least one embodiment with a leadless implantable heart stimulator, the absolute value of the acceleration signal may be integrated in each case over a cardiac cycle as a cyclical acceleration integral. In one or more embodiments, the acceleration signal may be recorded wideband. In at least one embodiment, when the patient is resting, the cyclical acceleration integral falls to a minimum value, which may be determined, for example exclusively, by the intrinsic heart movement and is approximately constant. In one or more embodiments, the minimum value may be stored and may be subtracted from the actual cyclical acceleration integral to compensate for the intrinsic heart movement. In at least one embodiment, the remaining integral represents the intensity of the body movement and may be used to adapt the stimulation rate.

Second Method Variant:

In the second method variant, according to at least one embodiment, the signed acceleration signal may be recorded. In one or more embodiments, in order to separate the two signal components, a mean value formation may be used, which adds up the signal over each individual complete cardiac cycle. In at least one embodiment, the positive and negative components of the acceleration signal of a cardiac cycle may be largely cancelled out. In one or more embodiments, the component of the intrinsic heart movement may be eliminated. In at least one embodiment, the remaining acceleration signal may be used to adapt the stimulation rate. In one or more embodiments, via the second method variant, the usable bandwidth of the body component of the acceleration signal may be limited upwardly by the heart rate. In at least one embodiment, the cardiac cycle may be determined in each case, easily, with the aid of the R waves.

According to one or more embodiments of the invention, the heart stimulator may include a housing placed intracardially or epicardially.

In at least one embodiment, the housing may include or may carry at least two electrodes, wherein each electrode may include an outwardly directed, electrically conductive surface. In one or more embodiments, the at least two electrodes may include stimulation electrodes, and may be electrically connected at least temporarily to the stimulation pulse generator via an electrical connection arranged in the interior of the housing and an electrical switching element. In at least one embodiment, electrically conductive components via which, for example, stimulation pulses may be delivered or electrical potentials may be detected are referred to herein as electrodes. In one or more embodiments, the electrodes, via their electrically conductive surface, may form poles to deliver the stimulation. In at least one embodiment, the electrodes may be integrated in the housing.

In one or more embodiments, the cardiac pacemaker may be arranged, for example, in the auricula of the heart accessible from the right atrium or directly in the ventricle. In at least one embodiment, the stimulation electrodes may be arranged on the surface of the pacemaker, and may stimulate at least the atrium or the ventricle as a self-sufficient device.

By way of one or more embodiments, at least one first electrode, or electrode pole, of the electrodes may include a very small surface area, such as a point-like surface, and wherein the surface area may be of less than 5 mm$^2$. In at least one embodiment, the first electrode may be arranged at a longitudinal end of the housing, wherein the housing may be an elongate housing. In one or more embodiments, the second electrode may include a small surface area, and for example may be of the same form as the first electrode discussed above. In at least one embodiment, both electrodes may be arranged in the immediate vicinity of one another at the same longitudinal end of the housing.

In one or more embodiments, the second electrode may be formed by or may include a large-area housing as part of the housing of the cardiac pacemaker and may form an indifferent pole, which acts as a neutral electrode.

In at least one embodiment, the electrodes may include or may be formed as ring electrodes, which run around the periphery of the housing. In one or more embodiments, the electrodes may be arranged close together. As such, in one or more embodiments, the exact orientation of the cardiac pacemaker following implantation, for example in the right atrial appendage or in the ventricle, may be relatively uncritical.

In at least one embodiment, the heart stimulator may be or may include a single-chamber demand pacemaker, such as an atrial single chamber pacing (AAI) pacemaker or a ventricular single chamber pacing (VVI) pacemaker. In at least one embodiment, the electrodes may be used as sensing electrodes, wherein the sensing electrodes may be connected at least temporarily to a detection stage in an interior of the housing.

In one or more embodiments, the heart stimulator may include a telemetry transmitter and a telemetry receiver, which are connected to the pacemaker controller. In at least one embodiment, the telemetry transmitter and the telemetry receiver may transmit operating data of the heart stimulator and may transmit recorded, physiological data, for example intracardial electrocardiograms, to an external device. In one or more embodiments, the telemetry transmitter and the telemetry receiver may receive programming and control commands. In at least one embodiment, operating parameters, for example a stimulation pulse intensity to be selected, may be determined via an external device and may be transmitted to the heart stimulator. As such, in one or more embodiments, the operating parameters may be stored in a corresponding memory of the pacemaker controller and may be used during operation of the pacemaker, which may be self-sufficient.

At least one embodiment may stimulate the right atrium, and for example the right or left ventricle, using the heart stimulator implanted in the heart. In one or more embodiments, the heart stimulator may include a wired or wireless interface, which is connected to the pacemaker controller. In at least one embodiment, the wired or wireless interface may exchange data with a corresponding interface of a second pacemaker, wherein the data includes data concerning or that correspond to the moments of events, such as natural or stimulated chamber contractions, occurring in a respective heart chamber. One or more embodiments may include a system formed of or that includes two or more heart stimulators. In at least one embodiment, one of the two or more heart stimulators may be placed in the atrium and another may be placed in the ventricle, wherein together both stimulators may function as or may be a dual-chamber pacemaker. In one or more embodiments, the atrial heart stimulator may transmit the moments of atrial events to the ventricular heart stimulator and vice versa. In at least one embodiment, the controller of each heart stimulator may respond to events in the other heart chamber, i.e. for example the ventricular heart stimulator may respond to atrial events, such that atrium-synchronous stimulation of the ventricle with physiologically adequate atrioventricular delay (AV interval) may be provided.

One or more embodiments of the invention may include more than two intracardially implantable heart stimulators as discussed above, such as a triple-chamber stimulation that provides resynchronization therapy, for example.

As discussed above, at least one embodiment of the invention may include a dual-chamber function device, such as heart stimulators connected to one another to provide data communication. One or more embodiments may include an electrode line for another heart chamber that may be connected to a heart stimulator to be placed in a heart chamber. In at least one embodiment, the electrode line may be flexible and may carry at least one stimulation electrode at its free end, such as the end that is not connected to the heart stimulator, or in the vicinity of the free end. In one or more embodiments, the electrode line may include a length that either allows a stimulation of the left ventricle via the coronary sinus, and, where appropriate, a lateral vein branching off therefrom, or protrudes through the right atrium into the right ventricle. At least one embodiment of the invention may include an electrode line that is to be introduced into the coronary sinus and into a lateral vein branching off from the coronary sinus. In one or more embodiments, the electrode line may be connected permanently to the housing of the cardiac pacemaker and includes an electrical conductor, which connects the stimulation electrode of the electrode lead to the stimulation pulse generator of the heart stimulator. As such, in at least one embodiment, the heart stimulator becomes a dual-chamber pacemaker, wherein to stimulate the heart chamber the heart stimulator may carry electrodes on its housing and includes the flexible electrode lead to stimulate the other heart chamber. In order to enable a dual-chamber stimulation, by way of one or more embodiments, the heart stimulator may include a single stimulation pulse generator connected alternately to the atrial stimulation electrodes and the ventricular stimulation electrodes. At least one embodiment of the invention may include two separate stimulation pulse generators for the atrium and the ventricle, which may be connected to a lead.

In one or more embodiments, the heart stimulator may include a circular cross section and wherein the housing thereof may be cylindrical at least over part of the length thereof. In at least one embodiment, the heart stimulator may include a battery of which the cross section thereof may be round and may use the housing volume to the best possible extent. As such, in one or more embodiments, the electrodes of the battery may be wound. In at least one embodiment, the battery volume may be between 1 cm$^3$ and 3 cm$^3$. In one or more embodiments, the battery capacity may be between 0.25 and 0.75 Ah.

In at least one embodiment, the housing may include or may be formed of housing elements that are welded to one another and that are made of metal. In one or more embodiments, at least one of the electrodes may be electrically insulated with respect to the welded metal housing. In at least one embodiment, one of the metal housing elements may be tubular with a closed base. In one or more embodiments, battery and control electronics may be inserted into the tubular housing element. As such, in at least one embodiment, the housing may be assembled from, for example, three housing elements, specifically from a central, tubular housing element and two end caps. In one or more embodiments, the stimulation and/or sensing electrodes may each be assembled and arranged between one of the housing caps and the central, tubular housing element.

In at least one embodiment, the housing elements may be made of or may include ceramic or plastic, and the electrodes may be formed by or may include metal rings.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
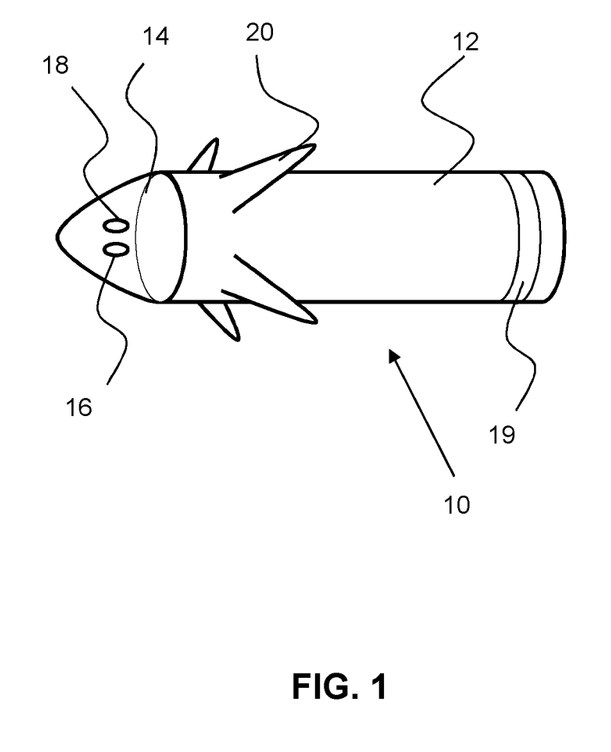
FIG. 1 shows an external view of a first variant of a heart stimulator, as a single-chamber cardiac pacemaker, to be implanted in the right atrial appendage or in the ventricle.

FIG. 1 shows a heart stimulator 10, according to one or more embodiments of the invention, as a single-chamber demand cardiac pacemaker. In at least one embodiment, the heart stimulator 10 may include an elongate, cylindrical housing 12 with a semi-spherical housing cap 14. One or more embodiments of the invention may include two stimulation electrodes 16 and 18 that include a small surface area, wherein the two stimulation electrodes 16 and 18 may be arranged at the tip of the housing cap 14. At least one embodiment includes fixing hooks 20 on the housing 12 in order to fix the heart stimulator 10 in a heart chamber, such as the ventricle 56 or also in the auricula of the right atrium.

In one or more embodiments, the housing 12 may be connected tightly to the housing cap 14, such that the space enclosed by the housing 12 and the housing cap 14 is hermetically sealed. In at least one embodiment, the electrodes 16 and 18 may be embedded in the housing cap 14 and may include electrically conductive surfaces, which are electrically insulated with respect to the rest of the housing 12 and may serve as poles to stimulate the heart tissue. In one or more embodiments, a far-field sensing electrode 19 may be provided as a ring electrode.

Figure 2:
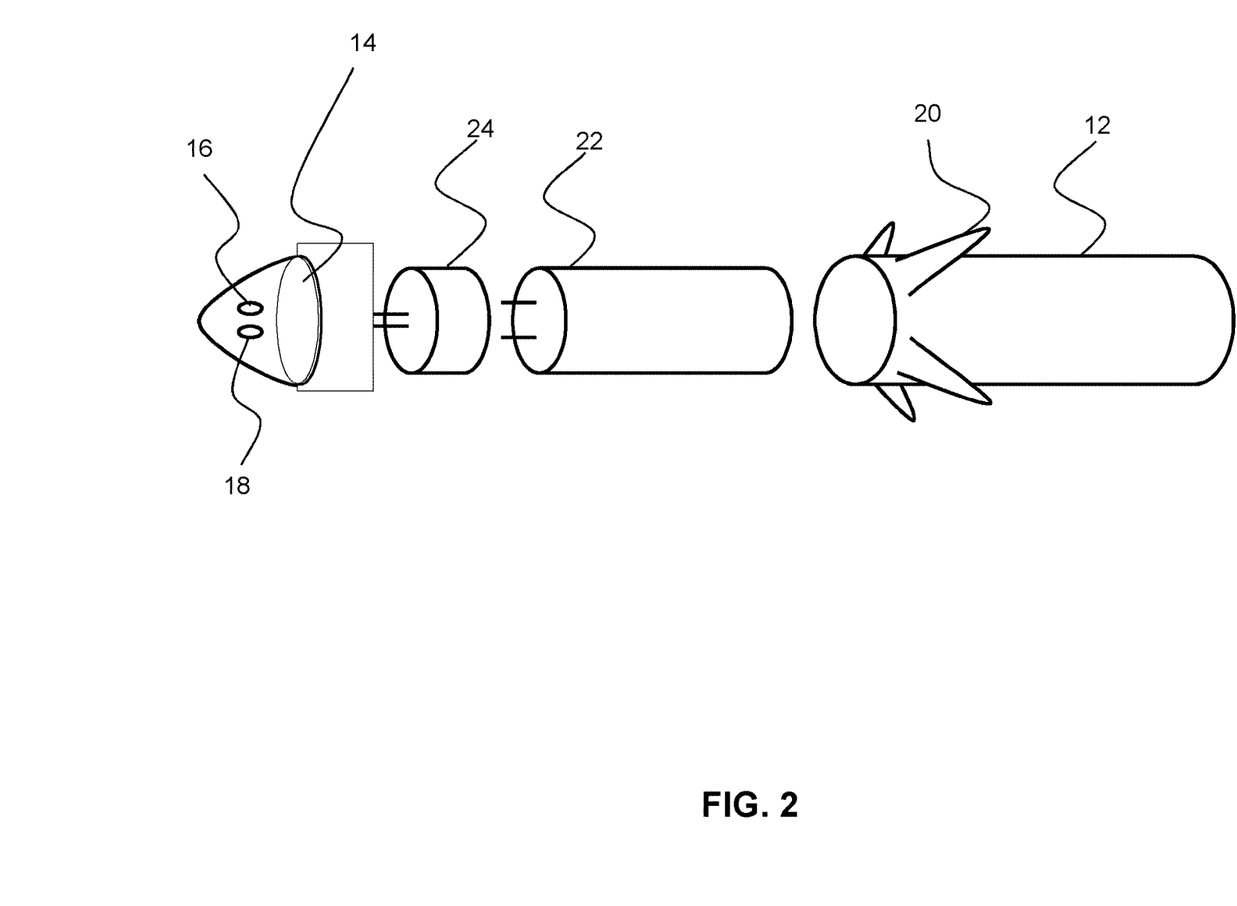
FIG. 2 shows a perspective exploded view of the heart stimulator from FIG. 1.

FIG. 2 is an exploded illustration of the heart stimulator 10 from FIG. 1 and shows the components arranged in the interior of the housing 12, including a battery 22 and an electronics module 24, according to one or more embodiments of the invention. In at least one embodiment, the electronics module 24 may include an electric pacemaker controller and at least one stimulation pulse generator. In one or more embodiments, the heart stimulator may be or may be used as a demand pacemaker, and may include a detection stage to detect heart signals as a sensing unit. In at least one embodiment, the stimulation pulse generator and the sensing unit may be electrically connected alternately to the two electrodes 16 and 18.

Figure 3:
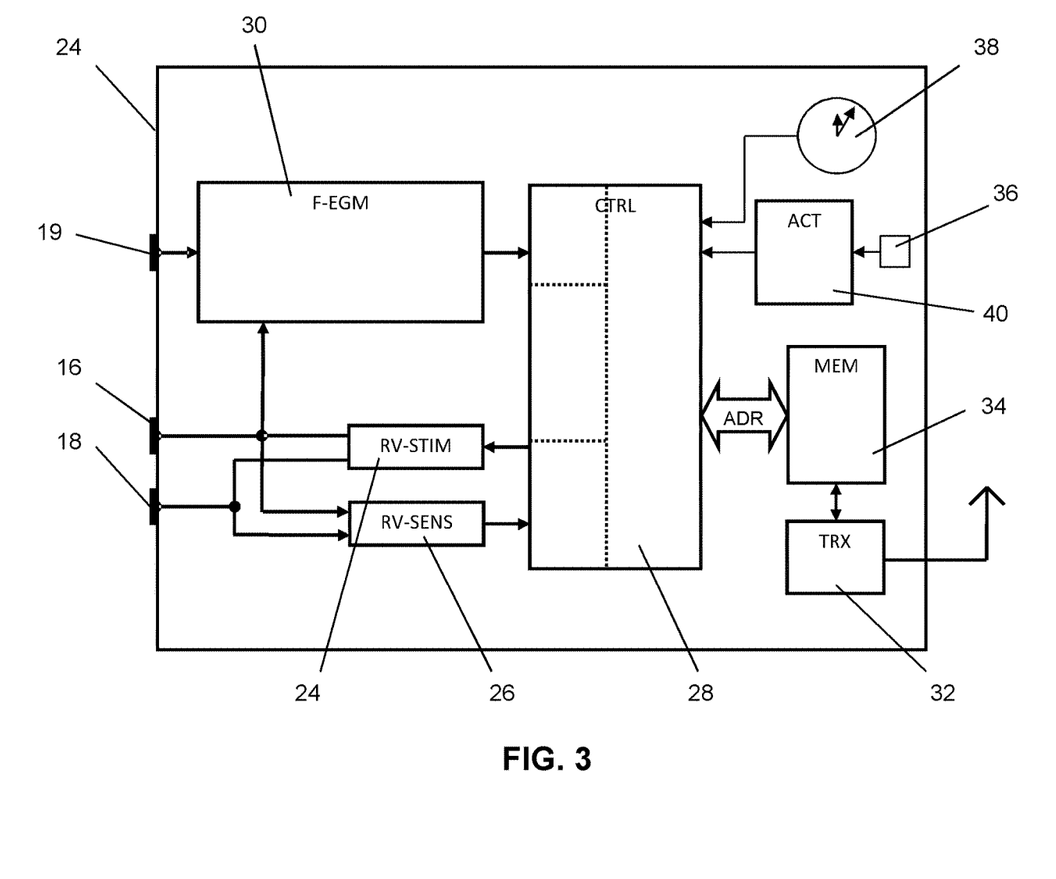
FIG. 3 shows a block diagram of the heart stimulator from FIGS. 1 and 2.

FIG. 3 schematically shows components of the electronics module 24, according to one or more embodiments of the invention.

In at least one embodiment, the electrodes 16 and 18 may each be connected both to a stimulation pulse generator 25 and to a sensing unit 26. In one or more embodiments, the heart stimulator 10 may be or may be used as a right-ventricular cardiac pacemaker, wherein the stimulation pulse generator 25 is a right-ventricular stimulation unit and the sensing unit 26 is a right-ventricular sensing unit. In at least one embodiment, the stimulation pulse generator 25 may provide the energy for a stimulation pulse and may deliver the stimulation pulse via the stimulation electrode 16 to adjacent tissue upon a trigger signal. In one or more embodiments, the stimulation pulse generator 25 may be connected to a control unit 28, which generates a corresponding trigger signal.

In at least one embodiment, the sensing unit 26 may detect local heart events via the electrodes 16 and 18, for example heart events that are to be assigned to the chamber arranged adjacently to the epicardial heart stimulator 10. In one or more embodiments, the heart stimulator 10 may be or may be used as a ventricular cardiac pacemaker, wherein the sensing unit 26 may detect right-ventricular events and may output a corresponding output signal to the control unit 28 in the case of detection of a respective ventricular event. As such, in at least one embodiment, the control unit 28 may trigger stimulation pulses only as required, specifically when the sensing unit 26 has not detected any intrinsic ventricular event.

By way of one or more embodiments, the far-field sensing electrode 19 may be connected to a far-field sensing unit 30, which is connected via a further input to the stimulation electrode 16. In at least one embodiment, the far-field sensing unit 30 may evaluate the potential difference between the far-field sensing electrode 19 and the stimulation electrode 16 as a far-field electrocardiogram. In one or more embodiments, the far-field sensing unit 30 may deliver an output signal to the control unit 28, which includes signal features such as signal atrial activity. In at least one embodiment, via the far-field sensing unit 30, the control unit 28 may detect, for example, atrial events when the heart stimulator 10 is used as a ventricular cardiac pacemaker and as such may be arranged for example adjacently to the right ventricle 56.

By way of one or more embodiments, an atrium-synchronous need-dependent rate-adaptive stimulation of the right ventricle 56 may be provided with the heart stimulator 10.

FIG. 3 shows, according to at least one embodiment of the invention, wherein the control unit may be connected to a memory unit 34, which may be used to store one or more of control signals and signal profiles recorded by the heart stimulator 10. In one or more embodiments, the heart stimulator 10 may include a telemetry unit 32 connected to the memory 34, such that the heart stimulator 10 may be reprogrammed and/or recorded signal profiles may be transmitted to an external device to be evaluated. In at least one embodiment of the invention, the control unit may be connected to an activity sensor 36, such as an acceleration sensor, such that a stimulation rate suitable for the metabolic need of a respective patient may be set. As such, one or more embodiments may include a rate-adaptive cardiac pacemaker. In at least one embodiment, the activity sensor 36 may include or may be an acceleration sensor, wherein the activity sensor 36 delivers an acceleration signal as an output signal, which is dependent on the metabolic need of a patient. In one or more embodiments, the control unit 28 may be connected to a timer unit 38.

In at least one embodiment, the heart stimulator 10 may include an activity determination unit 40, which processes the acceleration signal delivered from the activity sensor 36 and generates an activity signal from the acceleration signal.

In one or more embodiments, the activity determination unit 40 may perform one or more of the two following methods:

First Method Variant:

In at least one embodiment with a leadless implantable heart stimulator, the absolute value of the acceleration signal may be integrated in each case over a cardiac cycle as a cyclical acceleration integral. In one or more embodiments, the acceleration signal may be recorded wideband. In at least one embodiment, when the patient is resting the cyclical acceleration integral falls to a minimum value, which may be determined, for example exclusively, by the intrinsic heart movement and is approximately constant. In one or more embodiments, the minimum value may be stored and may be subtracted from the actual cyclical acceleration integral to compensate for the intrinsic heart movement. In at least one embodiment, the remaining integral represents the intensity of the body movement and may be used to adapt the stimulation rate.

Second Method Variant:

In the second method variant, according to at least one embodiment, the activity determination unit 40 may process the signed acceleration signal. In one or more embodiments, in order to separate the two signal components, a mean value formation may be used, which adds up the signal over each individual complete cardiac cycle. In at least one embodiment, the positive and negative components of the acceleration signal of a cardiac cycle may be largely cancelled out. In one or more embodiments, the component of the intrinsic heart movement may be eliminated. In at least one embodiment, the remaining acceleration signal may be used to adapt the stimulation rate. In one or more embodiments, via the second method variant, the usable bandwidth of the body component of the acceleration signal may be limited upwardly by the heart rate. In at least one embodiment, the cardiac cycle may be determined in each case, easily, with the aid of the R waves, which are in turn may be detected using the sensing unit 26.

Figure 4:
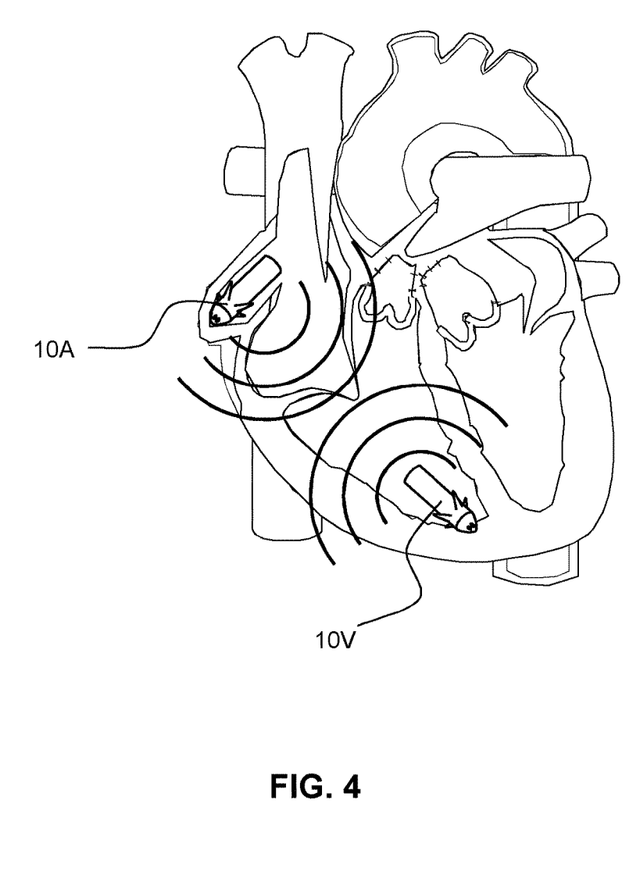
FIG. 4 shows a dual-chamber pacemaker system formed by two implanted cardiac pacemakers.

As discussed herein, in one or more embodiments, the electronics module 24 of a respective heart stimulator may include a wired or wireless interface to connect to and/or communicate with one or more further heart stimulators, for example further heart stimulators of the same type. As such, at least one embodiment may include two or more heart stimulators that together may form a multi-chamber pacemaker system, as shown in FIG. 4. FIG. 4 shows a dual-chamber system, according to one or more embodiments of the invention. In at least one embodiment, a first heart stimulator 10A may be arranged in the right auricula of the right atrium 52, and a second heart stimulator 10V may be arranged in the right ventricle 56 of the heart 50. In one or more embodiments, only one individual heart stimulator may be arranged in one chamber of a heart and for example may operate as a ventricular pacemaker in VVI mode or as atrial pacemaker in AAI mode.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

10 heart stimulator
10A first heart stimulator
10V second heart stimulator
12 housing
14 housing cap
16,18 stimulation and sensing electrodes
19 far-field sensing electrode
20 fixing hook
22 battery
24 electronics module
25 stimulation pulse generator
26 sensing unit
28 control unit
30 far-field sensing unit
32 telemetry unit
34 memory
36 acceleration sensor
38 timer unit
40 activity determination unit
50 heart
52 right atrium
56 ventricle

What is claimed is:

1. A leadless implantable heart stimulator comprising:
an acceleration sensor that delivers an acceleration signal as an output signal, wherein the acceleration sensor is configured to record intrinsic heart movements and body movements, wherein the acceleration signal comprises
a first component caused by an intrinsic heart movement of said intrinsic heart movements, and,
a second component caused by a body movement of said body movements, and,
an activity determination unit,
wherein the acceleration sensor is connected to the activity determination unit,
wherein the acceleration signal is a signed acceleration signal,
wherein the activity determination unit is configured to integrate the signed acceleration signal over a predefined period of time to form an activity signal, and,
a control unit and a stimulation unit connected to the control unit,
wherein the control unit is connected to the activity determination unit,
wherein the control unit is configured to control the stimulation unit based on a stimulation rate,
wherein the stimulation unit
comprises a stimulation pulse generator and a stimulation electrode, and
provides stimulation pulses based on the stimulation rate, and,
wherein the stimulation rate is dependent on the activity signal.

2. The heart stimulator as claimed in claim 1, wherein the activity determination unit is further configured to form the activity signal over a cardiac cycle.

3. The heart stimulator as claimed in claim 1, wherein the control unit is connected to the activity determination unit and is configured to detect rest phases.

4. The heart stimulator as claimed in claim 1, further comprising at least one sensing unit and at least one electrode, wherein the at least one sensing unit is connected to the at least one electrode and is configured to record electrical potential curves via the at least one electrode as an electrocardiogram (ECG) signal and to detect signal features of signal characteristics of the ECG signal that correspond to intrinsic heart actions.

5. An activity detection module comprising:
an acceleration sensor that delivers an acceleration signal as an output signal, wherein the acceleration sensor is configured to record intrinsic heart movements and body movements, wherein the acceleration signal comprises
a first component caused by an intrinsic heart movement of said intrinsic heart movements, and,
a second component caused by a body movement of said body movements; and,
an activity determination unit connected to the acceleration sensor,
wherein said acceleration signal is a signed acceleration signal,
wherein the activity determination unit is further configured to integrate the signed acceleration signal over a predefined period of time to form an activity signal, and,
a control unit and a stimulation unit connected to the control unit,
wherein the control unit is connected to the activity determination unit,
wherein the control unit is configured to control the stimulation unit based on a stimulation rate,
wherein the stimulation unit
comprises a stimulation pulse generator and a stimulation electrode, and
provides stimulation pulses based on the stimulation rate, and,
wherein the stimulation rate is dependent on the activity signal.

6. A method of forming an activity signal representing physical activity, comprising:
recording an acceleration signal using an acceleration sensor that delivers the acceleration signal as an output signal, wherein the acceleration sensor records intrinsic heart movements and body movements, wherein the acceleration signal comprises
a first component caused by an intrinsic heart movement of said intrinsic heart movements, and,
a second component caused by a body movement of said body movements,
integrating a signed acceleration signal over a predefined period of time to form an activity signal,
wherein said acceleration sensor is connected to an activity determination unit, and,
controlling a stimulation unit based on a stimulation rate using a control unit,
wherein the control unit is connected to the activity determination unit,
wherein the stimulation unit is connected to a control unit,
wherein the stimulation unit
comprises a stimulation pulse generator and a stimulation electrode, and
provides stimulation pulses based on the stimulation rate, and,
wherein the simulation rate is dependent on the activity signal.

* * * * *